United States Patent [19]

Esposito et al.

[11] 4,396,783

[45] Aug. 2, 1983

[54] HYDROXYLATING AROMATIC HYDROCARBONS

[75] Inventors: Antonio Esposito; Marco Taramasso; Carlo Neri, all of San Donato Milanese, Italy

[73] Assignee: Anic S.p.A., Palermo, Italy

[21] Appl. No.: 299,546

[22] Filed: Sep. 4, 1981

[30] Foreign Application Priority Data

Sep. 9, 1980 [IT] Italy .............................. 24547 A/80

[51] Int. Cl.³ .............................................. C07C 79/26
[52] U.S. Cl. .................................... 568/706; 568/653; 568/771; 568/803
[58] Field of Search ............... 568/706, 771, 803, 763, 568/650, 653

[56] References Cited

U.S. PATENT DOCUMENTS

| | | | |
|---|---|---|---|
| 3,445,526 | 5/1969 | Hooper | 568/771 |
| 3,580,956 | 5/1971 | Bloch | 568/771 |
| 4,045,896 | 8/1977 | Seifert et al. | 568/706 |
| 4,283,571 | 8/1981 | Keim et al. | 568/783 |

*Primary Examiner*—Werren B. Lone
*Attorney, Agent, or Firm*—Ralph M. Watson

[57] ABSTRACT

A process for the hydroxylation of aromatic hydrocarbons by hydrogen peroxide, consisting in reacting said compounds in the presence of synthetic zeolites which contain heteroatoms, both replaced and exchanged.

The reaction is carried out at a temperature comprised between 80° C. and 120° C. and in the presence of the hydrocarbon only or in the presence of a solvent which permits, at least partially, to admix the aromatic hydrocarbon with the hydrogen peroxide.

4 Claims, No Drawings

HYDROXYLATING AROMATIC HYDROCARBONS

This invention relates to an improved process for the hydroxylation of aromatic hydrocarbons, said process being performed by reacting the hydrocarbon concerned with hydrogen peroxide in the presence of synthetic zeolites.

The direct hydroxylation reaction of aromatic hydrocarbons with hydrogen peroxide is known long since and is carried out in the presence of a catalyst, which is generally selected from among the transition metal salts.

Such a reaction run, however, has a few defects among which the following are worth mentioning:

low selectivity towards hydrogen peroxide due to the partial decomposition thereof by metallic ions;

low selectivity towards the reacted hydrocarbons due to coupling reactions of intermediate organic radicals;

in the particular case of phenol, indeed, the biphenols which are formed are more probe to oxidation than phenol as such, that which is inevitably conducive to a considerable lowering of the conversion.

It is also known to employ, for performing the reaction between an aromatic hydrocarbon and hydrogen peroxide, an acidic aluminosilicate which has been either doped or partially modified by rare earth elements (U.S. Pat. No. 3,580,956).

The use of such a catalytic material, even admitting that it improves the performance of the methods aforementioned, does not permit, however, to offset in a complete way the production of considerable amounts of useless by-products, the presence of which has a negative bearing of the end results and the economy of the entire processing run.

The present applicants have now found, and this is the subject matter of the present invention, that it is possible to bind hydroxyls to aromatic rings by reacting the aromatic hydrocarbon concerned with hydrogen peroxide, without suffering from any of the shortcomings enumerated above by conducting the reaction in the presence of synthetic zeolites which contain heteroatoms, both replaced and exchanged.

Zeolite materials which can be employed in the process according to the present invention may be selected, for example, from among those disclosed in the U.S. patent application Ser. No. 046,923 filed June 8, 1979. This paper discloses a synthetic material composed of crystalline silica modified by the presence of elements which enter the crystalline lattice of silica so as to replace a few silicon atoms therein.

The modifying elements are selected from among Cr, Be, Ti, V, Mn, Fe, Co, Zn, Zr, Rh, Ag, Sn, Sb and B:

Said application relates also to the methods which permit to obtain such synthetic materials and reference is invited thereto for a scrutiny of the necessary details as well as for a better understanding of the structure of the material concerned.

Reverting now to the hydroxylation process which is the subject matter of the present application, it is important to emphasize the outstanding advantage stemming, in the performance of the process, from the use of synthetic zeolites, which lies in the possibility of directing the same reaction towards the formation of a product rather than of another by merely selecting a certain modified zeolite.

Thus, for example, in the case of hydroxylation of phenol, a synthetic material is employed which is crystalline, porous and composed of silicon and titanium oxides, and the use of such a material permits that a mixture of hydroquinone and pyrocatechol may be obtained in a ratio equal to or greater than 1.

The reaction between the aromatic hydrocarbon and hydrogen peroxide is carried out at a temperature selected in the range between 80° C. and 120° C., in the presence of the hydrocarbon alone, or also in the presence of a solvent permitting at least partially the miscibility with hydrogen peroxide. Thus, water, methanol, acetic acid, isopropanol and acetonitrile can be used.

Hydrocarbonaceous substrates which can be treated according to the present invention are: phenol, toluene, anisole, xylenes, mesitylene, benzene, nitrobenzene, ethylbenzene and acetanilide.

The method for preparing titanium silicalite (crystalline silica modified by titanium) comprises the preparation of a reaction mixture constituted by sources of silicon oxide and titanium oxide, and possibly an alkaline oxide, a nitrogenated organic base and water, having a reagent molar ratio composition as heretofore defined.

The silicon oxide source can be a tetraalkylorthosilicate, preferably tetraethylorthosilicate, or simply a silica in colloidal form, or again a silicate of an alkaline metal, preferably Na or K.

The titanium oxide source is a hydrolysable titanium compound chosen preferably from $TiCl_4$, $TiOCl_2$, and $Ti(alkoxy)_4$, preferably $Ti(OC_2H_5)_4$.

The organic base is a tatraalkylammonium hydroxide, in particular tetrapropylammonium hydroxide.

The reagent mixture is subjected to hydrothermal treatment in an autoclave at a temperature of between 130° and 200° C., under its own pressure, for a time of 1–50 hours until the crystals of the titanium silicalite precursor are formed. These are separated from the mother solution, carefully washed with water and dried.

In the anhydrous state they have the following composition: $xTiO_2 \cdot (1-x)SiO_2 \cdot \sim 0.04(RN^+)_2O$. The precursor crystals are heated for 1 to 72 hours in air at 550° C. in order to completely eliminate the nitrogenated organic base. The final titanium silicalite has the composition: $xTiO_2 \cdot (1-x)SiO_2$ where x is as heretofore defined.

The method for preparing the other modified crystalline silicas is the same as that for titanium silicalite.

A few examples will now be given, which aim at better illustrating the invention without limiting it in any wise.

Preparation of titanium modified crystalline silicas

EXAMPLE 1

This example illustrates the preparation of titanium silicalite with a high degree of purity.

455 g of tetraethylorthosilicate are placed in a pyrex glass vessel fitted with a stirrer and kept under a $CO_2$-free atmosphere, and 15 g of tetraethyltitanate are added followed gradually by 800 g of a 25% weight solution of tetrapropylammonium hydroxide (free from inorganic alkali). The mixture is kept stirred for about one hour, then heaing is commenced carefully in order to accelerate hydrolysis and evaporate the ethyl alcohol which is released.

After about 5 hours at 80°–90° C., the alcohol has been completely eliminated. The volume is increased to 1.5 liters with distilled water, and the opalescent homogeneous solution is transferred to a titanium autoclave fitted with a stirrer. The mixture is heated to 175° C., and is kept stirred at this temperature under its own pressure for a time of 50 hours. When the treatment is finished, the autoclave is cooled, the contents are discharged, and the mass of fine crystals obtained is recovered. This is carefully washed on a filter with hot distilled water many times.

The product is then dried and finally calcined at 550° C. for six hours.

EXAMPLE 2

This example illustrates the preparation of titanium silicalite using tetrapropylammonium peroxytitanate as the titanium oxide source.

The pertitanates are known to be stable in a strongly basic solution.

150 g of tetraethyltitanate are hydrolyzed by slowly dripping into 2.5 liters of distilled water under stirring. A white gelatinous suspension is obtained. It is cooled to 5° C. and 1.8 liters of 30% hydrogen peroxide, also cooled to 5° C., are added, then stirring occasionally over two hours while maintaining the temperature low. A clear orange-coloured solution is obtained. At this point, 2.4 liters of a 25% aqueous tetrapropylammonium hydroxide solution pre-cooled to 5° C. are added. After one hour, 500 g of Ludox colloidal silica containing 40% of $SiO_2$ are added, mixing is carried out carefully, and the mixture left standing overnight at ambient temperature. It is finally heated under stirring to 70°–80° C. for 6–7 hours. The mixture thus obtained is transferred to an autoclave, and the operations described in Example 1 are then carried out.

EXAMPLE 3

A 250-ml flask is charged with 52 g phenol (0.5532 mol), 0.5 g of titanium silicalite and 10 mls of 33% $H_2O_2$ (0.0988 mol) added dropwise. The reaction is carried out at a temperature of 120° C. and for a time of 90 minutes.

The results, as determined gaschromatographically are: 8.586% by wt of pyrocatechol plus hydroquinone with a ratio of pyrocatechol to hydroquinone equal to 0.9, 2.2% by wt of by-products, yield of hydrogen peroxide equal to 50%, selectivity of 80% relative to the useful products.

EXAMPLE 4

The procedure is the same as in Example 3, but the temperature is now 100° C. In this case the yield of $H_2O_2$ is 53%.

EXAMPLE 5

A 10-liter reactor is charged with 5,000 g of phenol, 392 g of 60% $H_2O_2$, 900 mls of water, 50 g of titanium silicalite and the reaction is carried out at 100° C.

The results are:
Yield hydroquinone to pyrocatechol+hydroquinone=57,53.
Yield in $H_2O_2$=53.3%.
By products: 21%.

EXAMPLE 6

A 100-ml flask is charged with 0.25 g of titanium silicalite, 26 mls of toluene, 1 ml of 60% $H_2O_2$ and the mixture is refluxed (also in the presence of an acid). After 3–5 hours there are separated 350 mg of ortho- and para-cresol, the principal product being para-cresol (75% of the total).

EXAMPLE 7

1.5 g of zeolite, 50 mls toluene, 10 mls of 36% $H_2O_2$, 0.8 ml of $H_2SO_4$ are charged in a 100-ml flask and refluxed. There are obtained 1,100 mg of ortho- and para-cresol with ratios equal to those of Example 6.

EXAMPLE 8

The procedure is the same as for Example 3 but using an equivalent amount of iron silicalite with 15 mls of water and maintaining the reaction temperature to 100° C. There are obtained 5.393 g of pyrocatechol plus hydroquinone with 70% pyrocatechol. Using as the catalyst chromium silicalite or vanadium silicalite there was obtained a ratio of pyrocatechol to hydroquinone equal to 60:40.

EXAMPLE 9

A cylindrical glass reactor, thermostatically controlled to 100° C., is charged with 80 mls anisole, 5 mls water and 4 g of titanium silicalite, whereafter there are introduced dropwise, with vigorous stirring and during 30 minutes, 10 mls of 36% $H_2O_2$ (by volume, equiv. to 106 millimols of $H_2O_2$). After 1½ hour at 100° C. $H_2O_2$ appears yo have been discharged. By gaschromatographical analysis there are found 2.144 g of guaiacol together with 4.712 g of hydroquinone monomethyl ether. The yield relative to $H_2O_2$ is 52.16% with an isomeric ratio ortho:para equal to 0.455, equivalent to 31.3% of ortho and 68.7% of para isomer.

EXAMPLE 10

A reactor as in Example 9 is charged with 60 mls of trimethylcarbinol and 20 mls nitrobenzene: 10 mls of 36% $H_2O_2$ (w/vol) are added dropwise at 100° C. with vigorous stirring. After 3 hours, $H_2O_2$ is discharged and there are identified, gaschromatographically, 3.871 g of ortho-nitrophenol, 0.752 g of meta nitrophenol and 2.516 g of para nitrophenol. The yield relative to $H_2O_2$ is 48.45% with an isomeric proportion ortho:meta:para of 5.15:1:3.35.

EXAMPLE 11

A 3-necked, 250-ml flask having a condenser and a stirrer is charged with 2.5 g of titanium silicalite 50 mls of toluene and 50 mls of trimethylcarbinol. There are now added 15 mls of 36% $H_2O_2$. On completion of the reaction, that which takes 3 hours approx., there is obtained a yield, relative to $H_2O_2$ of 20% and the isomeric distribution of the cresols is 12% for the ortho isomer, 7.5% for the meta isomer and 81.5% for the para isomer.

EXAMPLE 12

A 3-necked, 800-ml reactor equipped with a condenser and a stirrer, is charged, with 100 mls of methylisobutyl carbinol, 20 g of titanium silicalite and 20 mls of 36% $H_2O_2$, dropwise. There are obtained 6.5 g of cresols and the para isomer predominates (82%).

EXAMPLE 13

In a 500-ml flask, equipped with a condenser, there are added to 100 mls of toluene, 100 mls of diethylcarbonate (with stirring), 25 mls of water and 10 g of titanium silicalite. As the system is in thermal equilibrium, there are added dropwise 20 mls of 36% $H_2O_2$. There are obtained 4.2 g of cresols, with the following distribution: 55% orthocresol, 13% meta cresol and 32% para cresol.

EXAMPLE 14

A 500-ml flask is charged with 20 g of titanium silicalite, 100 mls of methylisobutyl ketone, 150 mls of toluene and 40 mls of water. There are added slowly during 2 hours approx., 40 mls of 36% $H_2O_2$. There are obtained 15.3 g of cresols with a selectivity of 72% for the para isomer.

EXAMPLE 15

A 500-ml flask is charged with 150 mls toluene, 100 mls methylisobutyl ketone, 40 mls of water and 20 g of titanium silicalite. To this slurry there are added 25 mls of 36% $H_2O_2$ while maintaining the temperature to 90° C. There are obtained 8.5 g of para cresol, 1.2 g of meta cresol, 1.9 g of ortho cresol, with a yield relative to $H_2O_2$ of 21%. 100 mls of such a solution are distilled and 4.2 g of cresols are obtained, with the following distribution of the isomers: 73.2% of para cresol, 10.34% of the meta isomer and 16.46% of the ortho isomer.

EXAMPLE 16

A 250-ml flask is charged with 50 mls of methylisopropyl ketone, 70 mls of toluene, 20 mls of water and 10 mls of 36% $H_2O_2$ (slowly added), 10 g of titanium silicalite. There are obtained 5.5 millimols of o-cresol (=13.7%), 3.2 millimol of m-cresol (=8.3%) and 31.2 millimol (=78%) of p-cresol, the yield relative to $H_2O_2$ being 41%.

EXAMPLE 17

10 g of the same catalyst as in Example 16, previously treated with $H_3PO_4$ and fired at 550° C., are placed in a 500-ml reactor together with 75 mls of toluene, 50 mls of methylisobutyl ketone and 20 mls of water. There are added 10 mls of 35% $H_2O_2$. There are obtained 0.712 g of ortho-cresol (=14.5%), 0.53 g of meta-cresol (10.8%) and 3.7 g of para-cresol (=75%), with a yield relative to $H_2O_2$ of 45%.

EXAMPLE 18

A 10-liter reactor equipped with a condenser and a stirrer is charged with 4,890 g of phenol, 920 g of demineralized water and 50 g of titanium silicalite. The mixture is heated to 98° C. As the system reaches its thermal equilibrium, there are added, by means of a metering pump, 576 g of 60% $H_2O_2$. On completion of the reaction there are obtained 603 g of pyrocatechol+-Hydroquinone corresponding to 5.486 mols of phenol with a yield relative to $H_2O_2$ of 54% and a selectivity in hydroquinone of 55%, the tar content being less than 20% and the selectivity towards phenol being 75%-80%.

Contrary to expectation, the tars formed during the reaction do not interact with the already formed hydroquinone and pyrocatechol: as a matter of fact, rectification tests of reaction mixture have confirmed, by weight basis analysis, the data reported above.

EXAMPLE 19

A 10-liter reactor as for the previous Example is charged with 4,255.8 g of phenol, 813 g of water and 42 g of titanium silicalite. As the system has reached its thermal equilibrium, there are added 675.2 g of 60% $H_2O_2$. After three hours of reaction there are obtained 250 g of pyrocatechol, 318 g of hydroquinone and 157 g of tarry by-products.

This solution has been subjected to rectification. The rectification step is carried out by treating 4,775 g of the raw product as follows.

Azeotropic water is distilled off by working with a vacuum of 240 Torr at 122° C. (temperature of the boiler). 1088 g of distillate are collected. The liquor is cooled to 60° C., the vacuum is brought back to 100 Torr and phenol is distilled up to 126° C. (boiler temperature). The distillate is 2,269.65 g whereas the residue in the boiler is 1,411.21 g.

1356 g of the residue are charged in the boiler of the rectification column; phenol is collected, at the outset, up to 213° C. (boiler temperature) and 152 Torr and, thereafter pyrocatechol up to 244° C. (boiler temperature) and 170 Torr, and, lastly, hydroquinone up to 260° C. (boiler temperature) and 155 Torr. From the gaschromatographic analysis of the several fractions which have been collected, there are obtained 256.56 g of pyrocatechol, 326.5 g of hydroquinone and 162 g of a tarry residue.

EXAMPLE 20

A 250-liter reactor equipped with a stirrer and a vapour abating column is charged with 170 kg of phenol, 24 kg of water, the titanium silicalite and 21.5 kg of 60% $H_2O_2$, these latter added by a metering pump as the temperature of the system is 100° C.

On completion of the reaction there ae added 11.22 kg of pyrocatechol, 13.99 kg of hydroquinone and 5.387 kg of tarry by-products. The yield relative to $H_2O_2$ is 60.4%.

We claim:

1. The process of hydroxylating an aromatic hydrocarbon selected from the group consisting of phenol, anisole, toluene and nitrobenzene, which comprises contacting said aromatic hydrocarbon with hydrogen peroxide in the presence of a catalyst in the temperature range between 80° C. and 120° C., said catalyst being a crystalline silica modified through the introduction into the crystalline lattice of the silica, as partial replacement of Si atoms therein, of metal selected from the group consisting of titanium, iron and vanadium.

2. The process of hydroxylating an aromatic hydrocarbon as claimed in claim 1, wherein said hydrocarbon is contacted with the hydrogen peroxide in the absence of a solvent.

3. The process of hydroxylating an aromatic hydrocarbon as claimed in claim 1, wherein said hydrocarbon is contacted with the hydrogen peroxide in the presence of a solvent adapted to render said hydrocarbon at least partially miscible with the hydrogen peroxide.

4. The process of hydroxylating an aromatic hydrocarbon as claimed in claim 3, wherein said solvent is a member of the group consisting of water, methanol, acetic acid, isopropanol and acetonitrile.

* * * * *